(12) United States Patent  (10) Patent No.: US 7,833,396 B2
Fukushima  (45) Date of Patent: Nov. 16, 2010

(54) BIOCHIP, BIOSENSOR AND INSPECTION SYSTEM

(75) Inventor: Hitoshi Fukushima, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 660 days.

(21) Appl. No.: 11/617,267

(22) Filed: Dec. 28, 2006

(65) Prior Publication Data

US 2010/0264024 A1    Oct. 21, 2010

(30) Foreign Application Priority Data

Jan. 13, 2006  (JP) .............................. 2006-006680

(51) Int. Cl.
*G01N 27/327* (2006.01)
(52) U.S. Cl. ............... 204/403.01; 422/82.01
(58) Field of Classification Search .......... 204/403.01–403.15; 422/82.01–82.03; 73/863, 73/863.31, 863.32, 864.81
See application file for complete search history.

(56) References Cited

U.S. PATENT DOCUMENTS

| | | | | |
|---|---|---|---|---|
| 5,407,554 | A * | 4/1995 | Saurer | 204/403.03 |
| 5,741,634 | A * | 4/1998 | Nozoe et al. | 204/403.03 |
| 6,413,213 | B1 | 7/2002 | Essenpreis et al. | |
| 6,753,144 | B1 * | 6/2004 | Hirota et al. | 435/6 |
| 7,208,077 | B1 * | 4/2007 | Albers et al. | 205/782 |
| 2003/0027219 | A1 * | 2/2003 | Ilsley et al. | 435/7.9 |
| 2005/0023137 | A1 * | 2/2005 | Bhullar et al. | 204/403.1 |

FOREIGN PATENT DOCUMENTS

| | | |
|---|---|---|
| DE | 103 29 820 B3 | 1/2005 |
| EP | 0 908 725 A1 | 4/1999 |
| EP | 1 507 146 A1 | 2/2005 |
| GB | 2 406 175 A | 3/2005 |
| JP | A 61-245051 | 10/1986 |
| JP | A-09-043189 | 2/1997 |
| JP | A-09-288079 | 11/1997 |
| JP | A-11-064270 | 3/1999 |
| JP | A-11-337514 | 12/1999 |
| JP | A 2000-033698 | 2/2000 |
| JP | A 2000-033712 | 2/2000 |
| JP | A 2001-242135 | 9/2001 |
| JP | A-2002-41654 | 2/2002 |
| JP | A-2003-322630 | 11/2003 |
| JP | A 2004-020238 | 1/2004 |
| JP | A 2005-077237 | 3/2005 |
| JP | A 2005-077287 | 3/2005 |
| JP | A 2005-084028 | 3/2005 |
| JP | A-2005-345243 | 12/2005 |
| WO | WO 88/00708 A1 * | 1/1988 |
| WO | WO 2004/083843 A1 | 9/2004 |
| WO | WO 2005/056824 A1 | 6/2005 |

OTHER PUBLICATIONS

F. Takagi et al. "Pico Liter Dispenser with 128 Independent Nozzles for High Throughput Biochip Fabrication" Micro Electro Mechanical Systems, 2004. 17$^{th}$ IEEE International Conference (MEMS) Maastricht Netherlands Jan. 25-29, 2004, XP010767879.

* cited by examiner

*Primary Examiner*—Alex Noguerola
(74) *Attorney, Agent, or Firm*—Oliff & Berridge, PLC

(57) ABSTRACT

A biochip, includes: an ink-jet head portion detachably mountable to a biosensor; a sensing electrode formed with a work electrode, a reference electrode, and a counter electrode; and a thin film transistor.

9 Claims, 6 Drawing Sheets

BIOCHIP, BIOSENSOR AND INSPECTION SYSTEM

BACKGROUND OF THE INVENTION

1. Technical Field

The present invention relates to a biochip, a biosensor and an inspection system. More particularly, the present invention relates to a biochip, a biosensor and an inspection system which can realize a micro device that is light, thin, short and compact in size, as well as high in performance and low in cost.

2. Related Art

Various methods are developed to inspect biologically-relevant materials such as DNA and protein to diagnose illness, detect individual difference in drug metabolism, and monitoring food, environment and the like.

For example, a gene detection chip comprising a pin electrode (refer to a first example of related art) and a protein analysis chip capable of detecting electrical signals (refer to a second example of related art) have been proposed.

Also, a manufacturing method of a biosensor providing an enzyme immobilized film by forming and immobilizing an enzyme film so as to deposit a polymer solution including a predetermined enzyme ejected from a nozzle to a surface of a predetermined sensor portion has been proposed (refer to a third example of related art).

Further, a manufacturing method of a sensor device forming high-density microelectrodes by printing a thin-film material solution on a microelectrode surface in microdots from an ink-jet nozzle has been proposed (refer to a forth example of related art).

JP-A-2001-242135 is the first example of related art.
JP-A-2004-20238 is the second example of related art.
JP-A-S61-245051 is the third example of related art.
JP-A-2000-33712 is the forth example of related art.

However, although various analysis chips and biosensors have been proposed as above, a micro device which can realize a high performance detection and inspection, light, thin, short and compact in size, and also low in cost was not proposed.

SUMMARY

The advantage of the present invention is to provide a biochip, a biosensor, and an inspection system which can realize a biosensing device that is light, thin, short and compact in size, as well as high in performance and low in cost.

With keen examination, those skilled in the art of the present invention has discovered to realize a biosensing device that is light, thin, short and compact in size, as well as high in performance and low in cost by adopting a predetermined biochip and/or a predetermined biosensor and completed the invention.

More specifically, the present invention includes (1) a biochip including an ink-jet head portion detachably mountable to a biosensor; a sensing electrode being formed with a work electrode, a reference electrode; and a counter electrode, and a thin film transistor; (2) the biochip according to (1) further including a well forming a concave portion to store a sample solution; and the sensing electrode being provided within the concave portion; (3) a biochip including an ink-jet head portion detachably mountable to a biosensor; a circular in form; and a plurality of sensing electrodes being formed with a work electrode, a reference electrode and a counter electrode being disposed along a circumference; (4) a biosensor including at least a storage portion storing a detachably mountable biochip; an ink-jet head portion discharging a sample solution by an ink-jet method; a controller controlling a discharge of liquid droplets from a nozzle; a memory accumulating analysis data of a biochip; a drive battery; and the ink-jet head portion having a cavity where a sample solution is supplied; a supply portion supplying the sample solution to the cavity; a plurality of nozzles being communicated to the cavity and disposed corresponding to each sensing electrode of the biochip; and a main body of a biosensor detachably mountable thereto; (5) the biosensor according to (4) further including a circuit board for RF tag; and (6) an inspection system including a biochip according to (1); or a biosensor according to (4).

The present invention can provide a biochip, a biosensor and an inspection system that is light, thin, short and compact in size, as well as high in performance and low in cost.

BRIEF DESCRIPTION OF THE DRAWINGS

The invention will be described with reference to the accompanying drawings, wherein like numbers reference like elements.

DESCRIPTION OF EXEMPLARY EMBODIMENTS

Next, embodiments of the present invention will now be described. Following embodiments are examples to explain the present invention and the invention is not limited only to the embodiments. The present invention may be practiced in various embodiments as long as they do not depart from the scope of the invention.

(Biochip)

A biochip of the present invention includes an inkjet head portion detachably mountable to a biosensor, a sensing electrode formed with a work electrode, a reference electrode and a counter electrode, and a thin film transistor.

Biochip According to a First Embodiment

Figure 1:
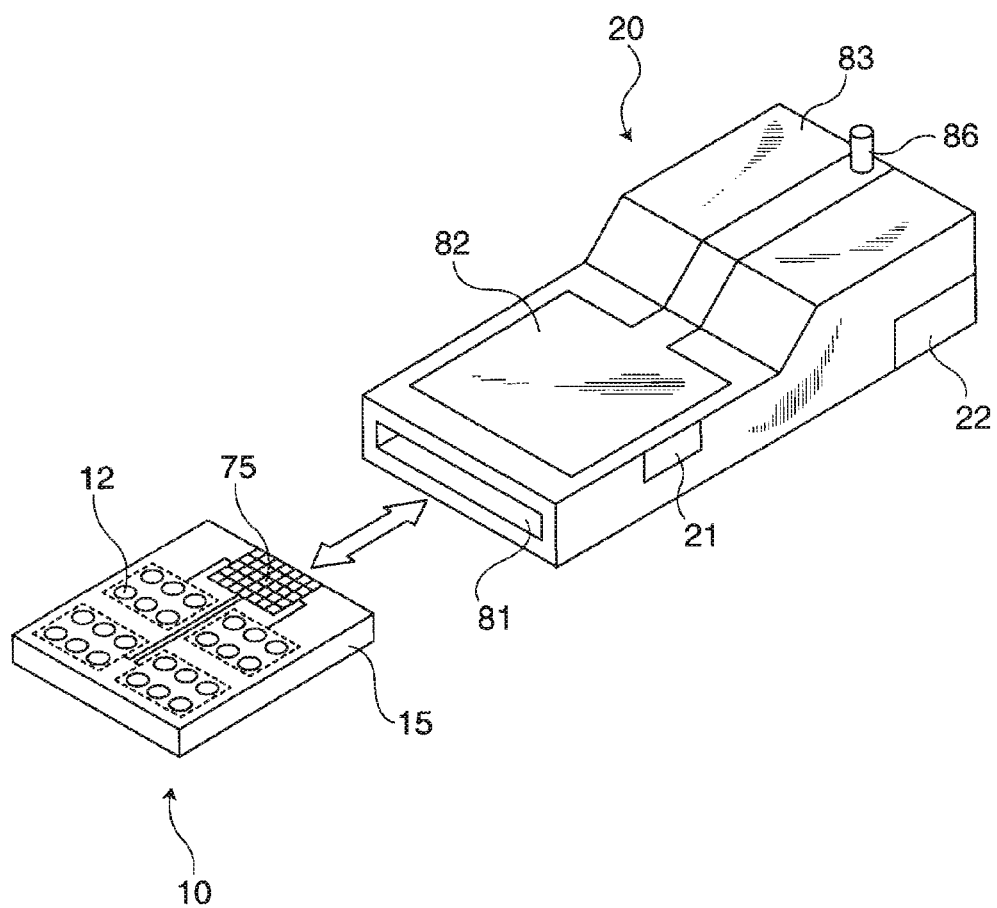
FIG. 1 is a diagram showing a relationship between a biochip and a biosensor according to a first embodiment.

FIG. 1 is a diagram showing a relationship between a biochip and a biosensor according to a first embodiment. As shown in FIG. 1, a biochip 10 is detachably mountable to a biosensor 20 and includes a plastic substrate 15, a plurality of sensing electrodes 12 formed on the above, and a thin film transistor (TFT) 75.

Figure 2:
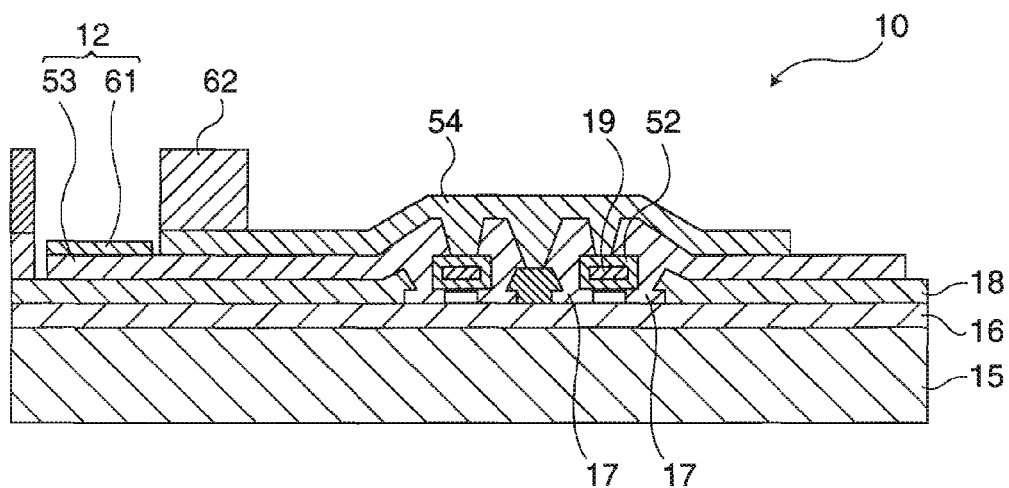
FIG. 2 is a partial cross section of the biochip according to the first embodiment.

FIG. 2 is a partial cross section of the biochip 10. As shown in FIG. 2, the biochip 10 includes the plastic substrate 15, an undercoat layer 16 laminated on the above, a source/drain regions 17 provided on the above, an insulating film 18, a gate electrode 19, a gate insulating film 52, a wiring layer 53, and a thin film transistor 75 formed with an insulating layer 54.

Further, the biochip 10 includes a plurality of wells 62 forming a concave portion to store a sample solution and a plurality of sensing electrodes 12 provided within each concave portion.

The sensing electrode 12 includes three wirings (not shown) of a work electrode (gold, for example), a reference electrode (Ag/AgCl, for example) and a counter electrode (carbon, for example), and an electrode pad 61 which takes out the wirings. The three wirings are provided in the wiring layer 53 and communicated to the thin film transistor 75 mounted on the biochip 10.

On a surface of the electrode pad 61, a biochemical reaction field is established so that specific reactions would take place efficiently to a living organism. Different kinds of biochemical reaction molecules may be fixed on a respective surface of each electrode pad 61, so as to monitor different biochemical reactions in parallel.

The above configuration can realize a biosensing device that is light, thin, short and compact in size, as well as high in performance and low in cost.

Further, as the biochip of the present invention is detachably mountable to the biosensor and low in cost, it may be used for disposables and for re-use.

(Biosensor)

A biosensor of the present invention includes at least a storage portion storing a detachably mountable biochip, an ink-jet head portion discharging a sample solution by an inkjet method, a controller controlling liquid droplets discharging from a nozzle, a memory accumulating analysis data of the biochip, a drive battery, and the ink-jet head portion having a cavity where a sample solution is supplied, a supply portion supplying the sample solution to the cavity, a plurality of nozzles communicated to the cavity and disposed corresponding to each sensing electrode of the biochip, and a main body of the biosensor detachably mountable thereto.

Biosensor According to the First Embodiment

As shown in FIG. 1, a biosensor 20 includes a main body 83 of a biosensor having a storage portion 81 storing a detachably mountable biochip 10, an ink-jet head portion 82 detachably mountable to the main body 83, a controller (not shown) provided in the main body 83 and controls discharge of liquid droplets from the ink-jet head portion 82, a memory (not shown) accumulating analysis data of the biochip, a drive battery 22, a circuit board 21 for RF tag and a supply portion 86 for a sample solution.

The drive battery 22 may be a solar battery or a hydrogen-powered battery. The memory, for example, is a flash memory.

Figure 3:
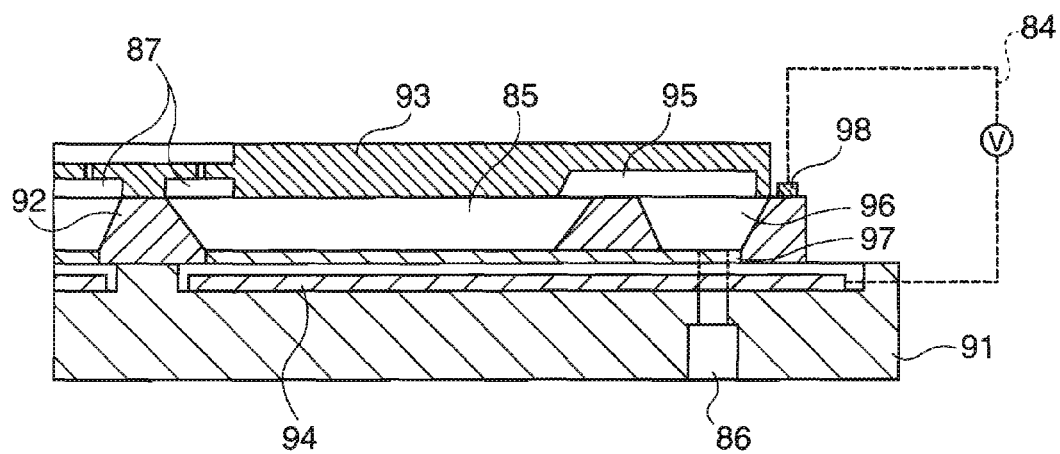
FIG. 3 is a schematic cross section of an ink-jet head portion of the biosensor according to the first embodiment.

FIG. 3 is a schematic cross-section of the ink-jet head portion 82. The ink-jet head portion 82 has a head structure called SEAJet® and can discharge a sample solution on demand by applying a voltage between electrodes using an electrostatically actuating method.

As shown in FIG. 3, the ink-jet head portion 82 includes a cavity 85 where a sample solution is supplied, the supply portion 86 supplying a sample solution to the cavity 85, 128 pieces of nozzles 87, a glass substrate 91, a silicon cavity substrate 92 including a cavity 85 and a vibrating plate 97, and a silicon nozzle substrate 93 including the nozzle 87. Each substrate 91, 92 and 93 is connected and manufactured by applying a MEMS process such as an anisotropic deep etching and a concentrated patterning etching.

The vibrating plate 97 is provided under the silicon cavity substrate 92, a fixed-depth concave portion is formed at a surface of the glass substrate 91 at a portion opposing to the vibrating plate 97, and an individual electrode 94 (indium tin oxide) is formed at a bottom of the concave portion. The vibrating plate 97 corresponding to the individual electrode 94 is opposed with a fixed gap.

128 pieces of nozzles 87 are disposed corresponding to each sensing electrode 12 of the biochip 10, and communicated to the cavity 85. The cavity 85 is a pressure chamber including the vibrating plate 97, and arranged in plurality towards a head-width direction (a direction perpendicular to a plane of FIG. 3) interposing a baffle (not shown) to each other.

A plurality of each cavity 85 is communicated to a common ink chamber 96, respectively through a path 95. The supply portion 86 for a sample solution is communicated to the common ink chamber 96.

A suitable sample solution is the one that biological substances such as enzyme, antibody, and functional protein are liquidized by buffer fluid, ethylene glycol and the like, and a body fluid such as blood, or derivative materials and the like which interact with biological molecules fixed on the electrode pad 61 of the biochip 10.

When a sample solution is supplied to the supply portion 86 by microsyringe and the like, and a driving voltage is applied between a common electrode 98 formed at an end portion of the silicon cavity substrate 92 and each individual electrode 94 by a drive control circuit 84, the vibrating plate 97 is displaced to the side of the individual electrode 94 by electrostatic force generated in between. When the driving voltage is blocked, pressure fluctuation generates to each cavity 85 as the vibrating plate 97 returns to the position before displacement by flexibility. Accordingly, the sample solution moves from the supply portion 86, to the common ink chamber 96, the path 95, the cavity 85, and the nozzles 87 and discharged from the nozzles 87. Microdroplets discharged from the nozzles 87 are discharged on each electrode pad 61 of the biochip 10.

The above configuration enables to realize a biosensing device that is light, thin, short and compact in size, as well as high in performance and low in cost.

Further, in the biosensor according to the present invention, the ink-jet head portion 82 is detachably mountable to the main body 83 of the biosensor, thereby enabling to be used for disposables and for re-use. Furthermore, as the main body 83 of the biosensor includes memory, current signals detected on the biochip 10 can be accumulated as analysis data, by going through a transistor amplifier circuit and an analog/digital conversion. Also, as it includes a circuit board 21 for RF tag, thereby enabling to sequentially transmit the analysis data accumulated in the memory to a host computer in wireless.

(Manufacturing a Biochip)

FIGS. 4A through 4G are an example of a manufacturing process of a biochip 10. The present manufacturing example uses SUFTLA (Surface Free Technology by Laser Ablation/Annealing) technology (registered trademark) which fabricates a low-temperature polycrystalline Si TFT on a plastic substrate by using a transfer process.

Figure 4:
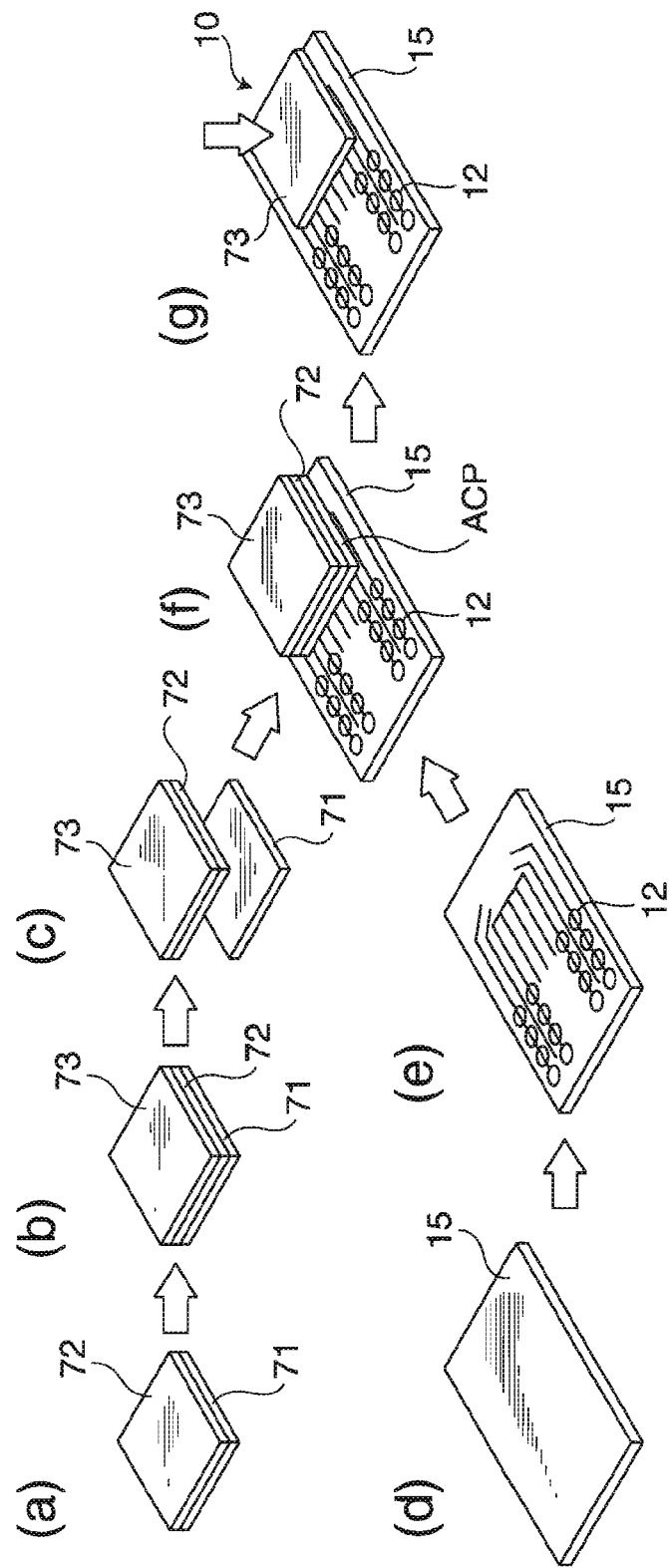
FIGS. 4A through 4G are diagrams showing an example of a manufacturing process of a biochip.

At first, as shown in FIG. 4A, a thin film transistor layer 72 is formed on a glass substrate 71. More specifically, after sequentially forming a sacrifice layer of amorphous Si, an $SiO_2$ undercoat layer 16, and a thin film transistor layer 72 on a quartz substrate, thereby forming the glass substrate 71 on the thin film transistor layer 72 by applying an aqueous adhesive. And then, by irradiating a XeCl excimer laser from below the quartz substrate, the quartz substrate and the sacrifice layer are separated from the undercoat layer 16.

Next, as shown in FIG. 4B, a plastic substrate 73 is formed on the thin film transistor layer 72 interposing an undercoat layer (not shown). More specifically, by applying a nonaqueous adhesive on the plastic substrate 73 formed of PES (polyethersulfone), the above-described undercoat layer 16 is bonded thereon.

Further, as shown in FIG. 4C, the glass substrate 71 is to be separated from the thin film transistor layer 72 by cleaning and dissolving the above-described aqueous adhesive.

Meanwhile, as shown in FIGS. 4D and 4E, a sensing electrode 12 made of an electrode pad and wirings is formed on the plastic substrate 15 by a screen printing. In the screen printing, three kinds of printing masks are made and printed, using different material patterns of three electrodes.

Next, as shown in FIG. 4F, a peeled surface of the thin film transistor layer 72 is aligned by temporary bonding on the plastic substrate 15, interposing an adhesive paste made of an anisotropic conductive paste (ACP). Further, as shown in FIG. 4G, the biochip 10 including a sensing electrode and a thin film transistor is obtained by compressing the temporary bonded body.

Biochip According to a Second Embodiment

Figure 5:
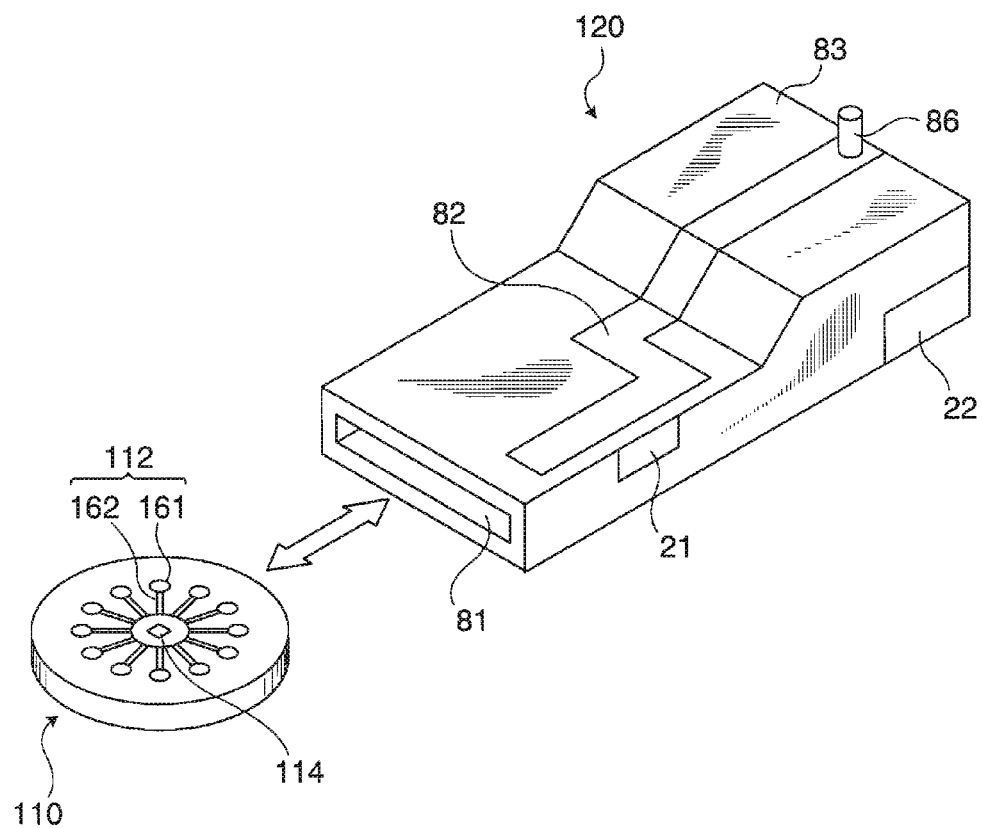
FIG. 5 is a diagram showing a relationship between a biochip and a biosensor according to a second embodiment.

FIG. 5 is a diagram showing a relationship between a biochip and a biosensor according to a second embodiment. As shown in FIG. 5, the only difference between the present embodiment and the biochip according to the first embodiment are that a biochip 110 is formed in circular, a thin film transistor 114 is disposed in a center, and a plurality of sensing electrodes 112 are disposed along the circumference.

As shown in FIG. 5, the plurality of sensing electrodes 112 are made of electrode pads 161 disposed along the circumference of the biochip 110, and three wirings 162 of a work electrode, a reference electrode and a counter electrode.

In the present embodiment, the biochip 110 is formed in circular, the thin film transistor 114 is disposed in the center, and a plurality of sensing electrodes 112 are disposed along the circumference, thereby enabling to mount the sensing electrodes 112 on a substrate efficiently as well as high in integration, even when there are many extended wirings as three wirings 162 extending from each electrode pad 161.

Biosensor According to the Second Embodiment

As shown in FIG. 5, in the present embodiment, a biosensor 120 has a storage portion 81 storing the detachably mountable biochip 110 in a circular-form. Further, the only difference from the biosensor according to the first embodiment is that the biosensor 120 has a rolling mechanism (not shown) to disk rotate the biochip 110, and includes a controller (not shown) which time synchronously controls the disk rotation and a discharge of a sample solution from a nozzle.

After the biochip 110 is mounted to the storage portion 81 and a sample solution is supplied to the supply portion 86, pressure fluctuation generates to a cavity by electrostatic force generated between a common electrode and each individual electrode, when a driving voltage is applied. Accordingly, the sample solution is supplied from a nozzle to an electrode pad 161 disposed along the circumference in a short period of time. While the sample solution is supplied, a disk rotation and a liquid discharge is time synchronously controlled so as liquid-droplets are properly discharged to each electrode pad 161 by rotating the biochip 110 in a circular disk-form. In the biosensor according to the present embodiment, as the biochip 110 in a circular disk-form rotates within the main body 83 of the biosensor, the nozzle may be one or plural.

The diameter of each electrode pad 161 is preferably 10.mu.m to 3 mm.

The above configuration can realize a micro device that is light, thin, short and compact in size, as well as high in performance and low in cost.

Further, in the biosensor of the present invention, as an ink-jet head portion 182 is detachably mountable to the main body 83 of the biosensor, it may be used for disposables and for re-use.

Furthermore, as a disk rotation and discharge of the biochip 110 is time synchronously controlled while supplying a sample solution, thereby enabling to supply and detect the sample solution efficiently.

Biochip According to a Third Embodiment

Figure 6:
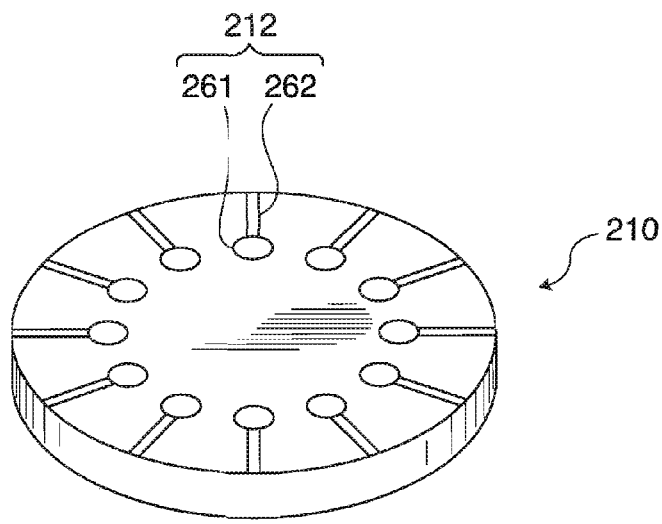
FIG. 6 is a diagram showing a biochip according to a third embodiment.

FIG. 6 is a diagram showing a biochip according to a third embodiment.

As shown in FIG. 6, in the present embodiment, the only difference from the biochip according to the above-described second embodiment is that a biochip 210 is not mounted with a thin film transistor, and three wirings 262 of a work electrode, a reference electrode and a counter electrode is a sensing electrode 212 which extends towards an outer circumference direction from an electrode pad 261.

When the one which has a connector portion designed in a shape to fit to an exterior of the biochip 210 and a transistor circuit is used as a biosensor, thereby setting the biochip 210 in the connector portion, making an analysis possible, as it is directly connected to the transistor circuit of the biochip main body from the connector portion.

In the present embodiment, as the biochip 210 is in a circular-form and the plurality of sensing electrodes 212 are disposed along a circumference, even when many extended wirings as three wirings 262 are extending from each electrode pad 261, the sensing electrode 212 can be mounted on a substrate efficiently and high in integration.

Further, as in the case of the second embodiment, because a disk rotation and a discharge of the biochip 210 are time synchronously controlled while sample solution is supplied to the biochip 210, the sample solution can be supplied and detected efficiently (Inspection System)

An Inspection System of the Present Invention Includes the Above-Described biochip and the above-described biosensor.

By the above configuration, an inspection system according to the present invention can realize a biosensing device that is light, thin, short and compact in size, as well as high in performance and low in cost.

Meanwhile, in the first through third embodiments, the case using a combination of the specific-structured biochip and the specific-structured biosensor was described, but the present invention is not limited to this, but also includes inspection systems only with the specific-structured biochip, only with the specific-structured biosensor, or the one biosensors and biochip of other structures are combined therewith.

Examples

Hereinafter, the present invention is to be described in further detail using examples, but the present invention is not limited to these embodiments. Those skilled in the art can practice not only examples hereinafter described but also capable of practicing with various changes, and such changes are included within the scope of the claim.

At first, a plurality of electrode pads 61 of a biochip 10 according to the first embodiment was configured with a gold electrode, and the surface of the gold electrode was coated with a thiol self-assembled monolayer (SAM) having a PEG chain.

Next, 50.mu.m of sample solution including 10 units of glucose dehydrogenase (GDH) enzyme molecule, 2 mM of ferrocenecarboxylic acid as a mediator, 10.1M of KC and 10 mM of PBS buffer is mounted on respective four gold electrodes coated with SAM and respectively add a fixed amount of glucose solutions (1 mM, 5 mM, 10 mM, 15 mM and 20 mM).

Then, a sample solution of the same composition as above except including 10 units of glucose oxidase (GOx) in place of 10 units of GDH, is mounted on respective different four gold electrodes coated with SAM, and further added 5 mM of glucose solution.

Next, a reaction current caused by electrons generated by an oxidation reaction was detected. The measurement was simultaneously processed at each electrode independently, and results of a plurality of enzyme reactions were obtained as a data in a short period of time. A CV curve was made by sweeping an applied voltage at each electrode, for example, from −0.3V to 0.5V at a speed of 50 mV/sec, thereby evaluating the reaction of each electrode by its peak current value. The evaluation was made by taking an average of measured values from four electrodes.

For example, in a case when 1 mM of glucose solution was added to GDH sample solution, an average value of current density at the electrode area of four electrodes was $2.1 \times 10^2$.mu.m $A/cm^2$.

Figure 7A:
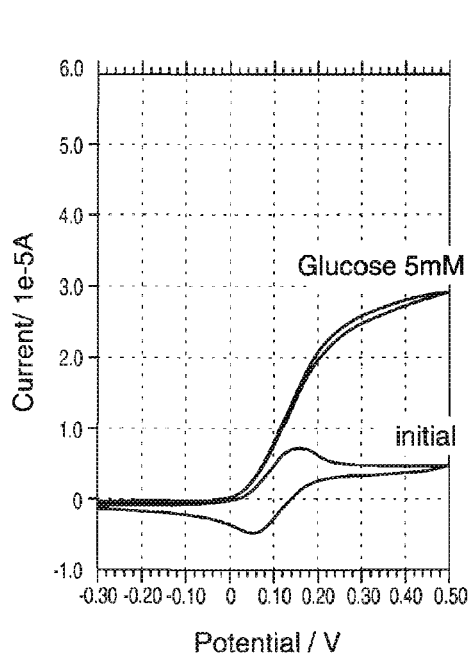
FIGS. 7A and 7B are examples showing a relationship between potential and current value.
Figure 7B:
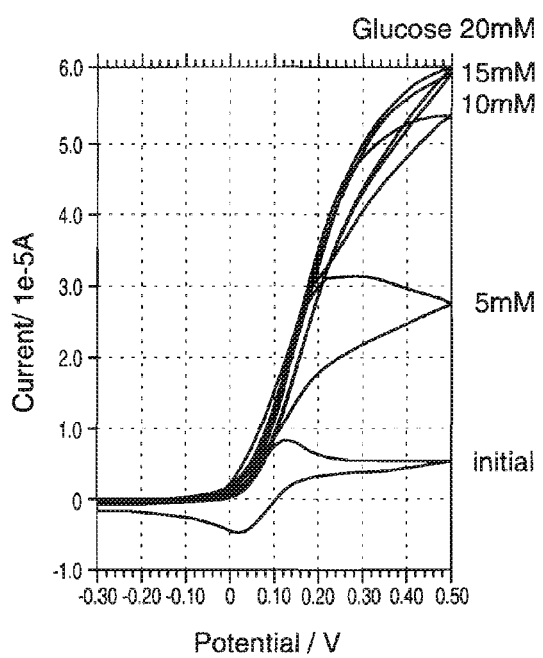

The results of these measurements are shown in FIGS. 7A and 7B. As shown in FIGS. 7A and 7B, the current value increases with the rise of potential.

Meanwhile, a measurement method is not limited to the above, but a pulse voltammetry method (applied potential is fixed, for example at 0.5V) may be used to measure the change of reaction current with time and perform velocity analysis.

Further, each electrode may be fixed to an electrode surface by mixing 0.5% of denatured BSA by weight and 2% of glutaraldehyde by weight with enzyme molecule to the above composition. In such a case, the electrode surface is coated with SAM which an end is modified with an amino group.

What is claimed is:
1. A biochip, comprising:
   a work electrode;
   a reference electrode;
   a counter electrode;
   an electrode pad, biochemical reaction molecules being fixed on a surface of the electrode pad; and
   a thin film transistor,
   a first portion of the work electrode, a first portion of the reference electrode, a first portion of the counter electrode, and the electrode pad being included in a sensing electrode section,
   a second portion of the work electrode, a second portion of the reference electrode, and a second portion of the counter electrode being included in a wiring section, and
   the wiring section electrically connecting the sensing electrode section and the thin film transistor.
2. The biochip according to claim 1, further comprising:
   a well forming a concave portion storing a sample solution, wherein the sensing electrode section is provided within the concave portion.
3. A biochip, comprising:
   a plurality of groups of sensing electrodes disposed along an edge of the biochip, the biochip having a circular shape,
   each of the plurality of groups of sensing electrodes including a work electrode, a reference electrode, a counter electrode, and an electrode pad,
   biochemical reaction molecules being fixed on a surface of the electrode pad, and
   one of the work electrode, the reference electrode, and the counter electrode being disposed between the electrode pad and a substrate.
4. A biosensor, comprising:
   a storage portion storing a detachably mountable biochip, the biochip including at least one sensing electrode;
   an ink-jet head portion discharging a sample solution by an ink jet method;
   a controller controlling a discharge of a liquid droplet from a nozzle;
   a memory accumulating analysis data of the biochip;
   a drive battery; and
   the ink jet head portion, the ink-jet head portion including:
      a cavity where the sample solution is supplied;
      a supply portion supplying the sample solution to the cavity;
      a plurality of nozzles, one of the plurality of nozzles connected to the cavity, the plurality of nozzles disposed corresponding to each of a plurality of sensing electrodes of the biochip; and
      a disk rotator that rotates the biochip while the sample solution is discharged,
      the ink-jet head portion being detachably mounted to a main body of the biosensor.
5. The biosensor according to claim 4, further comprising:
   a circuit board for an RF tag.
6. An inspection system, comprising:
   the biosensor according to claim 5.
7. The biosensor according to claim 4, further comprising:
   a circuit board that communicates with an RF tag.
8. An inspection system, comprising:
   the biosensor according to claim 7.
9. An inspection system, comprising:
   the biosensor according to claim 4.

* * * * *